(12) United States Patent
Teitelbaum

(10) Patent No.: US 11,850,142 B2
(45) Date of Patent: Dec. 26, 2023

(54) METHODS OF MANUFACTURING A Y-SHAPED BRANCH POINT FLOW DIVERSION DEVICE AND METHODS OF DEPLOYING A Y-SHAPED BRANCH POINT FLOW DIVERSION SYSTEM

(71) Applicant: THRU-FLO ENDOVASCULAR, INC., Santa Monica, CA (US)

(72) Inventor: George P. Teitelbaum, Santa Monica, CA (US)

(73) Assignee: THRU-FLO ENDOVASCULAR, INC., Santa Monica, CA (US)

( * ) Notice: Subject to any disclaimer, the term of this patent is extended or adjusted under 35 U.S.C. 154(b) by 0 days.

(21) Appl. No.: 17/399,946

(22) Filed: Aug. 11, 2021

(65) Prior Publication Data

US 2021/0378813 A1 Dec. 9, 2021

Related U.S. Application Data

(63) Continuation of application No. PCT/US2021/036468, filed on Jun. 8, 2021.
(Continued)

(51) Int. Cl.
*A61F 2/06* (2013.01)
*A61F 2/90* (2013.01)
(Continued)

(52) U.S. Cl.
CPC .................. *A61F 2/06* (2013.01); *A61F 2/90* (2013.01); *A61F 2/954* (2013.01);
(Continued)

(58) Field of Classification Search
CPC .... A61F 2/06; A61F 2/90; A61F 2/954; A61F 2002/065; A61F 2002/068;
(Continued)

(56) References Cited

U.S. PATENT DOCUMENTS 5,669,924 A * 9/1997 Shaknovich ............ A61F 2/958
606/198
6,033,435 A 3/2000 Penn et al.
(Continued)

FOREIGN PATENT DOCUMENTS

CA 2294735 A1 1/1999
WO 2021252529 A1 12/2021

OTHER PUBLICATIONS

PCT/US2021/036468 , Invitation to Pay Additional Fees and, Where Applicable, Protest Fee, dated Aug. 17, 2021, 2 pages.
(Continued)

*Primary Examiner* — Christie Bahena
(74) *Attorney, Agent, or Firm* — Dorsey & Whitney LLP

(57) ABSTRACT

A flow diversion device for treating branch point aneurysms that includes a wire stent frame comprising a plurality of wire elements, the wire stent comprising a proximal limb and two distal limbs, wherein the proximal limb and the two distal limbs converge at a crotch of the wire stent frame. The plurality of wire elements may be braided together. The flow diversion device may have a substantially Y-shape or T-shape. The flow diversion device may be manufactured by using two tubular flow diversion devices to make a Y-shaped flow diversion device.

9 Claims, 10 Drawing Sheets

Related U.S. Application Data

(60) Provisional application No. 63/036,711, filed on Jun. 9, 2020.

(51) Int. Cl.
*A61F 2/954* (2013.01)
*A61F 2/95* (2013.01)
*B29D 23/00* (2006.01)
*A61F 2/82* (2013.01)

(52) U.S. Cl.
CPC ... *A61F 2002/065* (2013.01); *A61F 2002/068* (2013.01); *A61F 2002/823* (2013.01); *A61F 2002/9505* (2013.01); *A61F 2002/9511* (2013.01); *A61F 2210/0014* (2013.01); *A61F 2240/001* (2013.01); *B29D 23/003* (2013.01)

(58) Field of Classification Search
CPC ........ A61F 2002/823; A61F 2002/9505; A61F 2002/9511; A61F 2210/0014; A61F 2240/001; A61F 2210/001; B29D 23/003
See application file for complete search history.

(56) References Cited

U.S. PATENT DOCUMENTS

| | | | |
|---|---|---|---|
| 6,197,049 B1 | 3/2001 | Shaolian | |
| 6,322,587 B1 | 11/2001 | Quiachon et al. | |
| 6,325,822 B1* | 12/2001 | Chouinard | D04C 3/48 |
| | | | 623/1.15 |
| 6,582,394 B1 | 6/2003 | Reiss et al. | |
| 8,690,907 B1 | 4/2014 | Janardhan et al. | |
| 9,474,640 B2 | 10/2016 | Johnson | |
| 2001/0007954 A1* | 7/2001 | Shaolian | A61F 2/07 |
| | | | 623/1.11 |
| 2003/0135259 A1* | 7/2003 | Simso | A61F 2/954 |
| | | | 623/1.12 |
| 2006/0079952 A1* | 4/2006 | Kaplan | A61F 2/97 |
| | | | 623/1.11 |
| 2006/0095118 A1 | 5/2006 | Harley | |
| 2006/0190070 A1 | 8/2006 | Dieck et al. | |
| 2007/0270902 A1 | 11/2007 | Slazas et al. | |
| 2008/0097495 A1 | 4/2008 | Feller, III et al. | |
| 2008/0194994 A1* | 8/2008 | Bown | A61M 25/09 |
| | | | 148/559 |
| 2009/0259286 A1* | 10/2009 | Ohri | A61F 2/958 |
| | | | 623/1.11 |
| 2010/0274339 A1* | 10/2010 | Muzslay | A61F 2/97 |
| | | | 623/1.11 |
| 2011/0077730 A1* | 3/2011 | Fenster | A61F 2/97 |
| | | | 623/1.23 |
| 2012/0324696 A1* | 12/2012 | Liu | A61F 2/97 |
| | | | 604/103.05 |
| 2014/0194970 A1* | 7/2014 | Chobotov | A61F 2/966 |
| | | | 623/1.12 |
| 2014/0249620 A1 | 9/2014 | Carman et al. | |
| 2015/0005868 A1 | 1/2015 | Koskas et al. | |
| 2016/0199204 A1 | 7/2016 | Pung et al. | |
| 2017/0007432 A1* | 1/2017 | Dorn | A61F 2/962 |
| 2019/0380852 A1* | 12/2019 | Eker | A61F 2/07 |
| 2019/0388213 A1 | 12/2019 | Torrance et al. | |
| 2020/0121444 A1 | 4/2020 | White et al. | |
| 2021/0161644 A1 | 6/2021 | Teitelbaum | |

OTHER PUBLICATIONS

PCT/US2021/036468, International Search Report and Written Opinion, dated Oct. 26, 2021, 10 pages.
U.S. Appl. No. 16/954,487, Non-Final Office Action, dated Sep. 29, 2021, 14 pages.
PCT/US2018/066048, International Search Report and Written Opinion, dated Apr. 3, 2019, 13 pages.

* cited by examiner

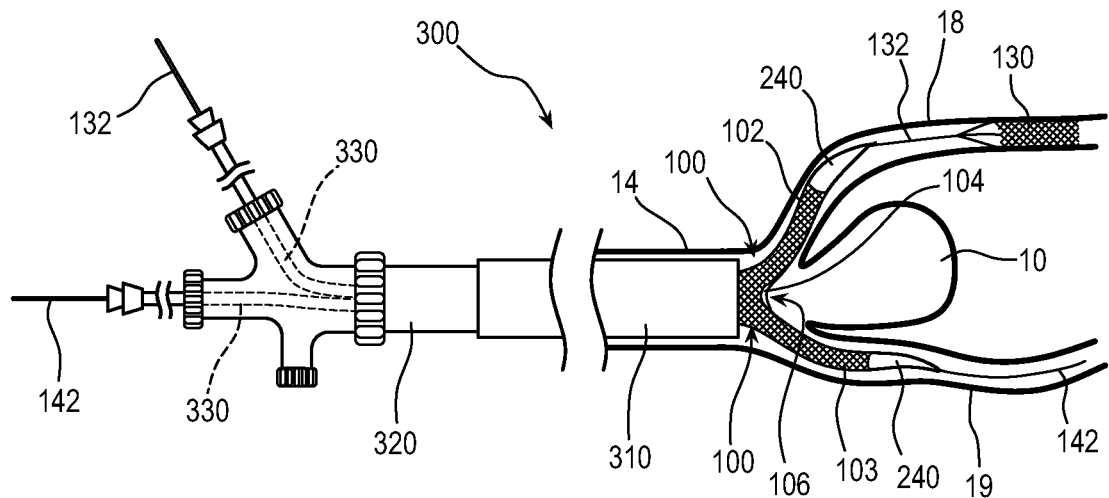
FIG. 22
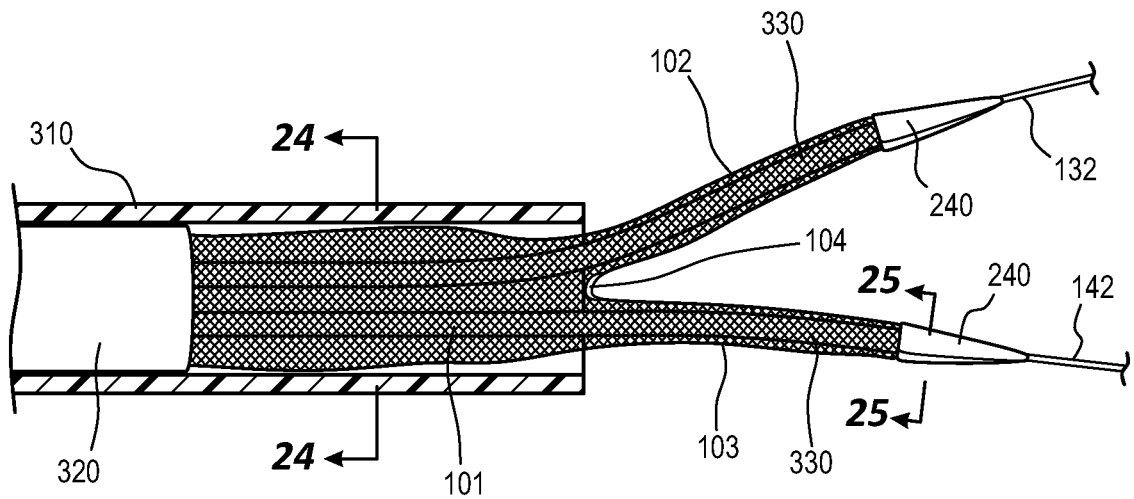
FIG. 23
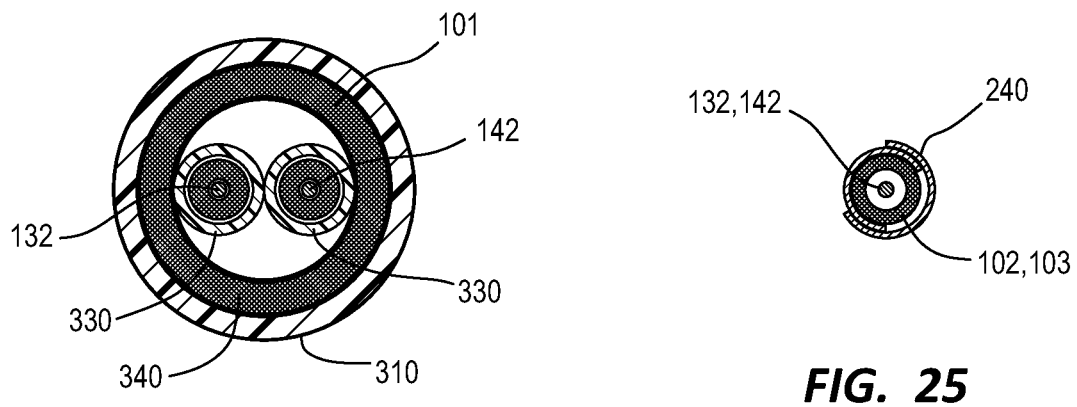
FIG. 24
FIG. 25

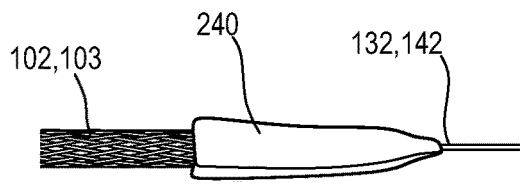 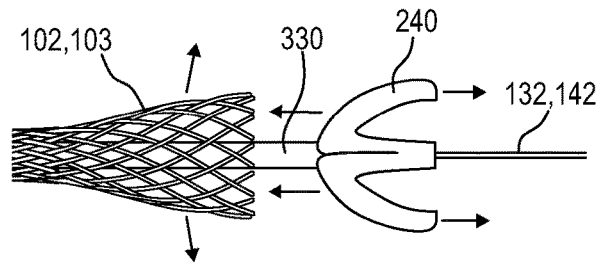
FIG. 26          FIG. 27
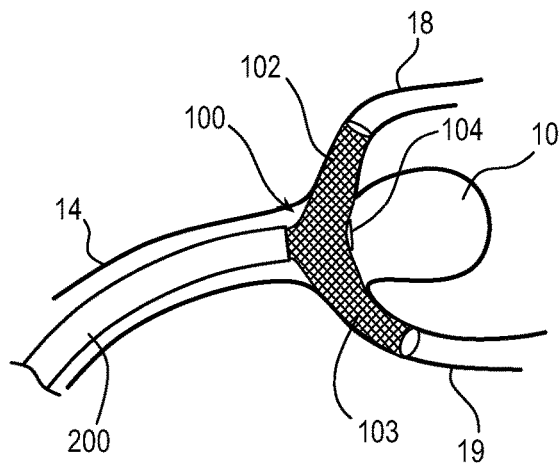 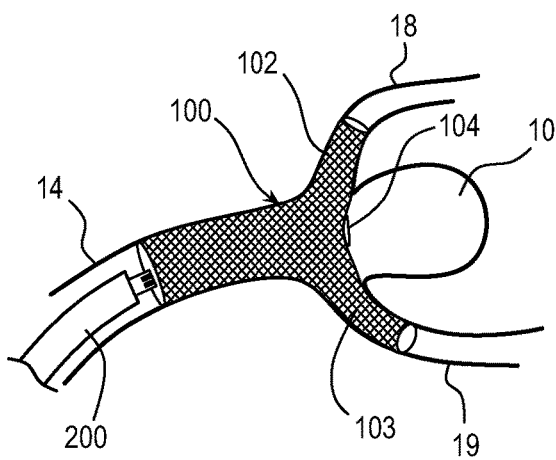
FIG. 28          FIG. 29
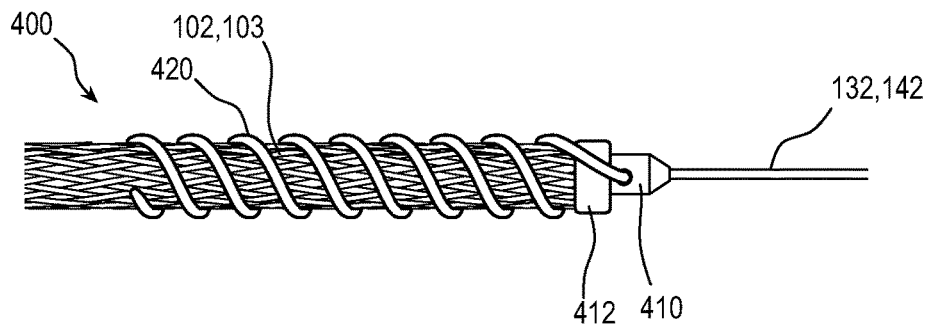
FIG. 30

METHODS OF MANUFACTURING A Y-SHAPED BRANCH POINT FLOW DIVERSION DEVICE AND METHODS OF DEPLOYING A Y-SHAPED BRANCH POINT FLOW DIVERSION SYSTEM

RELATED APPLICATIONS

This application is a continuation of and claims priority to International Patent Application No. PCT/US2021/036468, filed Jun. 8, 2021, which claims the benefit of U.S. Provisional Application No. 63/036,711, filed Jun. 9, 2020, each of which is incorporated by reference herein in its entirety.

TECHNICAL FIELD

The field of the present disclosure relates generally to medical devices, and in particular, to flow diversion devices that may be used for treatment of wide-neck and fusiform aneurysms.

BACKGROUND

Flow diversion devices, such as the Pipeline™ embolization device and the Surpass Streamline® flow diverter, are stent-like devices composed of tightly braided, thin-wire elements typically used for the treatment of intracranial aneurysms. These devices are employed endovascularly to treat aneurysms by diverting blood flow away from the aneurysm to induce aneurysm thrombosis, which helps prevent rupture of the aneurysm and may eventually result in the gradual shrinkage and occlusion of the aneurysm. In addition, when used for fusiform aneurysms (i.e., aneurysms with no definable neck), the flow diversion device may promote reconstruction of a smooth endothelial covered channel in continuation with the parent artery. While the flow diversion device directs blood away from the aneurysm, the thin-wire braided design allows modest through-flow of blood to maintain the patency of important small arterial side branches adjacent to the treated aneurysm.

Large intracranial aneurysms (which range in diameter from 10-25 mm) and particularly giant intracranial aneurysms (those greater than 25 mm in diameter) frequently have a wide-neck (dome-to-neck diameter ratio of less than 2) or are fusiform. Typically, large and giant aneurysms have poor occlusion, rupture, and survival rates regardless of the form of therapy (e.g., open brain surgery or other endovascular techniques) used to treat them. The use of finely braided stent devices to divert blood flow away from aneurysms has yielded promising treatment results compared to open surgery and other conventional endovascular techniques, such as coil embolization with or without the assistance of an endovascular stent or balloon remodeling.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 22 illustrates a Y-shaped flow diversion deployment device according to one embodiment of the present disclosure.

FIG. 23 illustrates a cross section view of the Y-shaped flow diversion deployment device of FIG. 22.

FIG. 24 illustrates a cross section end view of a guide catheter of the Y-shaped flow diversion device of FIG. 22.

FIG. 25 illustrates a cross section end view of a guide catheter of the Y-shaped flow diversion device of FIG. 22.

FIG. 26 illustrates a side detailed view of one of two distal limbs of a Y-shaped flow diversion device constrained by a circumferential flap according to one embodiment of the present disclosure.

FIG. 27 illustrates a side detailed view of one of two distal limbs of a Y-shaped flow diversion device of FIG. 27 unconstrained by the circumferential flap.

FIG. 28 illustrates the deployment of a Y-shaped flow diversion device at a branch point aneurysm according to one embodiment of the present disclosure.

FIG. 29 illustrates the deployment of the Y-shaped flow diversion device of FIG. 28 with the device expanded and foreshortened to treat the branch point aneurysm.

FIG. 30 illustrates one of two distal limbs of a Y-shaped flow diversion device being secured and constrained to the distal end of a delivery microcatheter or flexible hypotube by a wire coiled around the distal limb according to one embodiment of the present disclosure.

DETAILED DESCRIPTION

With reference to the drawings, this section describes particular embodiments and their detailed construction and operation. The embodiments described herein are set forth by way of illustration only and not limitation. The described features, structures, characteristics, and methods of operation may be combined in any suitable manner in one or more embodiments. In view of the disclosure herein, those skilled in the art will recognize that the various embodiments can be practiced without one or more of the specific details or with other methods, components, materials, or the like. For the sake of clarity and conciseness, certain aspects of components or steps of certain embodiments are presented without undue detail where such detail would be apparent to those skilled in the art in light of the teachings herein and/or where such detail would obfuscate an understanding of more pertinent aspects of the embodiments.

Tubular braided-wire flow diversion devices are self-expanding, flexible endovascular implants that have been used in hundreds of thousands of cerebral aneurysm patients world-wide with great success. These tubular flow diverters (the Pipeline™ and Surpass Streamline® devices) divert blood flow past side-wall aneurysms causing them to shrink and occlude. However, the small amount of blood flow through the interstices between the crisscrossing wires is sufficient to maintain patency of important cerebral side branches. Although aneurysms may also be treated with surgical clipping and coil embolization, both of these techniques are plagued with delayed aneurysm recanalization.

Other newer devices, such as the WEB® embolization system, are designed to create flow diversion within the aneurysm sac. However, like with any intrasaccular device, there is the risk of aneurysm perforation during the device placement.

Figure 1:
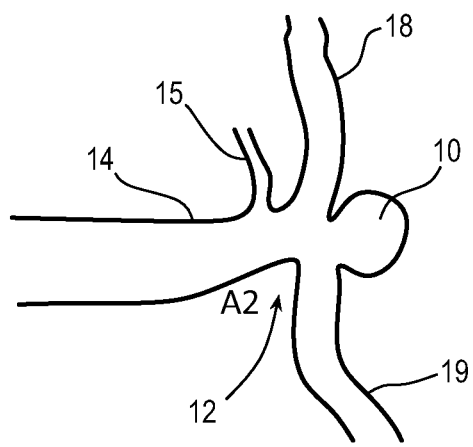
FIG. 1 illustrates a branch point aneurysm.
Figure 2:
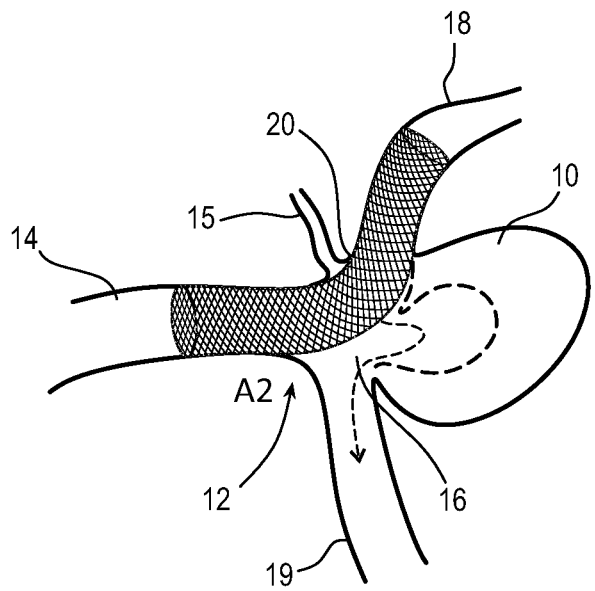
FIG. 2 illustrates an example flow diversion device positioned at a branch point aneurysm.

Certain aneurysms located at a major branch point cannot be readily treated with a flow diverter. FIG. 1 illustrates an aneurysm 10 located at the branch point 12 of a vessel 14 with two runoff arteries 18, 19. FIG. 1 also illustrates a side branch 15. FIG. 2 illustrates branch point aneurysm 10 that is being treated with a tubular braided-wire flow diversion device 20. The aneurysm neck 16 is not completely sealed by the tubular braided-wire flow diversion device 20 thus allowing blood flow to the sac of the aneurysm 10 and thus keeping the aneurysm 10 patent.

Figure 3:
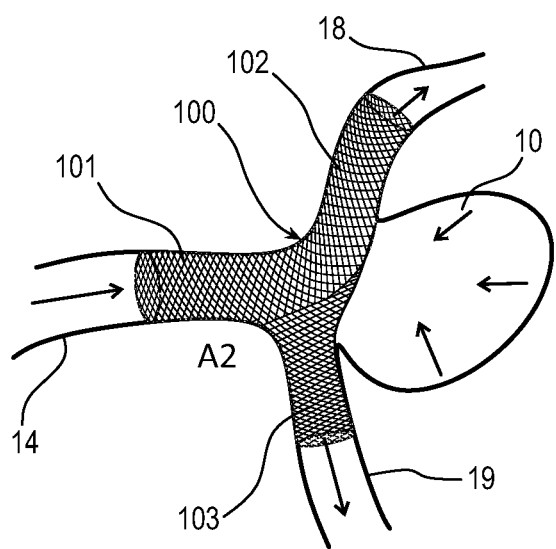
FIG. 3 illustrates a Y-shaped flow diversion device positioned at a branch point aneurysm according to one embodiment of the present disclosure.
Figure 4:
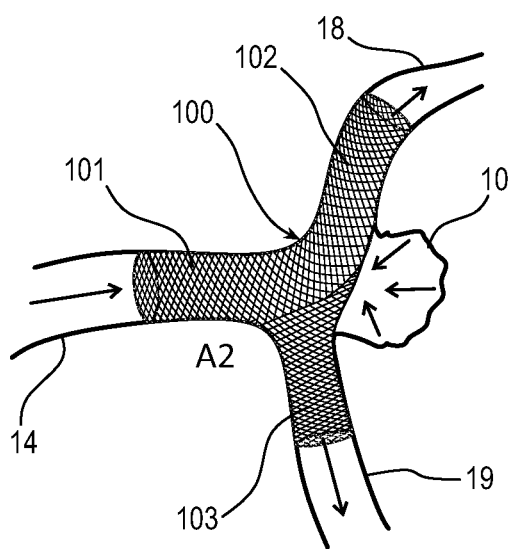
FIG. 4 illustrates the Y-shaped flow diversion device of FIG. 3 positioned at a branch point aneurysm three to six months after deployment of the Y-shaped flow diversion device.

FIGS. 3-4 illustrate the process of shrinking a branch point aneurysm 10 with a Y-shaped flow diversion device 100 fabricated with braided wire, with two distal limbs 102, 103 extending into the two runoff arteries 18, 19 of the branch point 12. FIG. 3 illustrates the flow diversion device 100 deployed and expanded at the branch point 12. The flow diversion device 100 may stagnate the flow of blood to the aneurysm 10, but maintain patency of side branches. After a period of time, such as six months, the aneurysm 10 may shrink as illustrated in FIG. 4.

One example of the use of the Y-shaped flow diversion device 100 may be a wide-neck aneurysm at the junction among the A2 segment of the anterior cerebral artery as shown in FIG. 1, the origin of the internal frontal branches, and the pericallosal artery. Once the two distal flow diverter limbs 102, 103 are positioned at the origin of the internal frontal branches and the pericallosal artery, a proximal limb 101 is deployed within the A2 segment. Flow diversion may lead to flow stagnation within the aneurysm cavity 10 (a dead-end sack) and eventual involution of this structure. Other examples where use of the Y-shaped flow diversion device 100 may be useful would be a basilar tip of an ICA terminus wide-neck aneurysm.

Figure 5A:
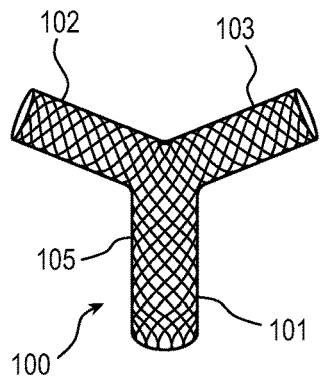
FIG. 5A illustrates a Y-shaped flow diversion device according to one embodiment of the present disclosure.
Figure 5B:
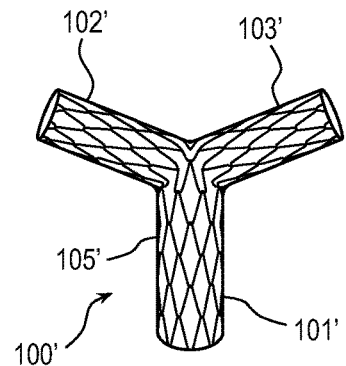
FIG. 5B illustrates a Y-shaped flow diversion device according to one embodiment of the present disclosure.
Figure 6:
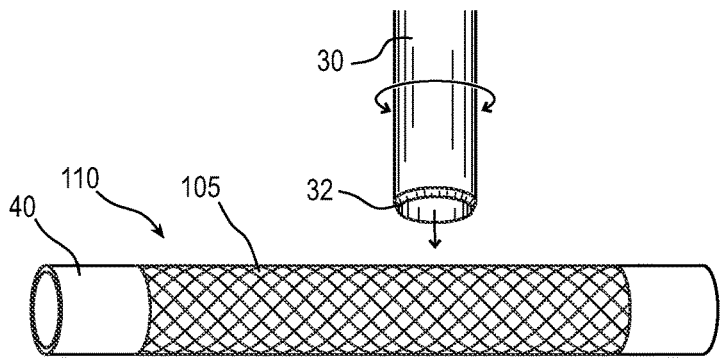
FIG. 6 illustrates a process of creating a hole or round cut-out from a first tubular flow diversion device to make a Y-shaped flow diversion device according to one embodiment of the present disclosure.

FIGS. 5A and 5B illustrate embodiments of branch point wide-neck aneurysm flow diversion devices. The flow diversion devices of FIGS. 5A and 5B may be applied to arterial branch points, such as brain arteries. FIG. 5A illustrates a flow diversion device 100 that may be substantially Y-shaped having a proximal limb 101 and two distal limbs 102 and 103. The distal limbs 102,103 may be at an angle relative to the proximal limb 101. In some embodiments, the flow diversion device 100 may be more T-shaped than Y-shaped, in that the two distal limbs 102 and 103 are substantially perpendicular to the proximal limb 101. The angle of the distal limbs 102, 103 may range between 15 degrees and 90 degrees.

The Y-shaped flow diversion device 100 may comprise a wire stent frame. The wire stent frame may be in the form of a braided-wire device with a plurality of wire elements 105. The braided-wire design for the Y-construct may be a self-expanding woven Nitinol wire design with a myriad of tiny closed wire cells with less than 0.5 mm cell diameter that would be small enough to create stagnation of flow within a branch point aneurysm but would allow just enough flow to keep side branches and perforators patent such as the side branch 15 of FIG. 1. In some embodiments, the wire elements 105 may have a diameter than 0.001 inches. In some embodiments, the wire elements 105 may be fabricated between 0.0008 and 0.0017 inch diameter having about 75% chromium-cobalt alloy and 25% platinum-tungsten alloy wires. Each limb 101, 102, and 103 may have 40 to 80 wires. Two of the limbs 102 and 103 of the flow diversion device 100 may extend underneath a wide-neck saccular aneurysm 10 into distal branch vessels 18, 19 (see FIGS. 2-4). The proximal limb 101 of the flow diversion device 100 may anchor the flow diversion device 100 within the proximal parent vessel 14 of the branch point aneurysm 10. In some embodiments, the Y-shaped flow diversion device 100 may be self-expanding.

FIG. 5B illustrates a Y-shaped flow diversion device 100' comprising a plurality of wire elements 105' that form a zigzag self-expanding wire stent (fabricated from Nitinol, for example, and having a wire diameter of approximately 0.001 inch). The wire elements 105' form the proximal limb 101' and the distal limbs 102' and 103'.

The Y-shaped flow diversion device 100 may be fabricated in a number of different ways. For example, the Y-shaped flow diversion device 100 may be fabricated on a mandrel utilizing a braiding process with a single layer of braided wires, the Y-shaped flow diversion device 100 being a single piece. In some embodiments, additional layers of braided wires may be utilized. Another process would be to utilize a couple of tubular braided-wire flow diversion devices to form the Y-shaped flow diversion device 100.

FIGS. 7-13 illustrate a process of manufacturing or fabricating a Y-shaped flow diversion device 100 using two tubular braided-wire flow diversion devices. The process begins with a first tubular braided-wire diversion device 110 and a second tubular braided-wire flow diversion device 120. Each tubular braided-wire flow diversion device 110, 120 may comprise 48 wires braided together. However, as discussed above, the number of wires may vary between 40 and 80 wires. A majority of the wires are fabricated from a cobalt-chromium alloy. In some embodiments, every fourth wire is fabricated form a radiopaque platinum-tungsten material.

Figure 7:
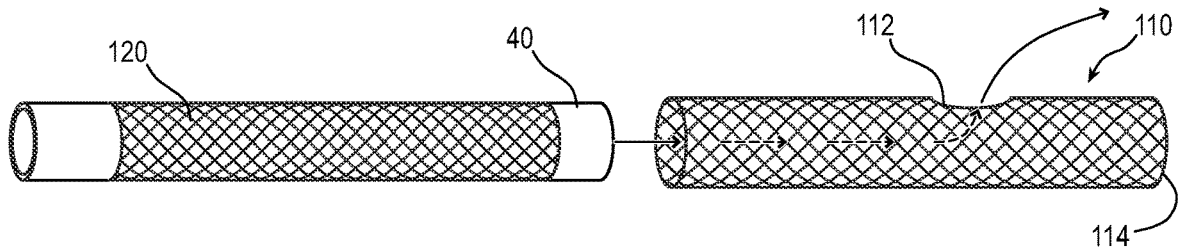
FIG. 7 illustrates inserting a second tubular flow diversion device through a hole in the first tubular flow diversion device of FIG. 7 to make a Y-shaped flow diversion device according to one embodiment of the present disclosure.

FIG. 7 illustrates a hole 112 or a round cut-out made in the first braided-wire diversion device 110 with a cutting device 30 (e.g., metallic tube) with a sharp end 32. The hole 112 is disposed a predetermined distance from a distal end 114 of the first device 110. A plastic tube 40 is placed in the lumen of the first device 110 to provide a support to the first device 110. The sharp end 32 of the cutting device 30 is pressed against the first device 110 and is rotated to cut a hole 112 in the first device 110. The plastic tube 40 serves as a support to the first device 110 when the hole 112 is cut into the first device 110. The hole 112 may also be formed in other manners. The diameter of the hole 112 may be substantially the same as the diameter of the expanded first device 110 and/or the second device 120. In some embodiments, the diameter of the hole 112 is smaller than the diameter of the expanded first device 110. In some embodiments, the diameter of the hole 112 is bigger than the diameter of the expanded first device 110.

Figure 8:
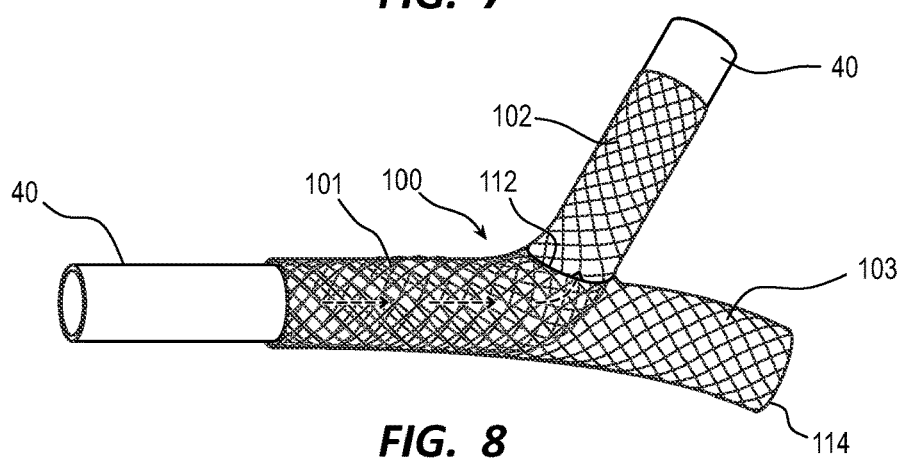
FIG. 8 illustrates the Y-shaped flow diversion device formed with the first and second tubular flow devices.

FIG. 8 illustrates the second device 120 being inserted into the first device 110 and pulled through the hole 112 of the first device 110. After the hole 112 is made in the first device 110, the plastic tube 40 may be removed from the first device 110. The plastic tube 40 or another plastic tube may be placed in a lumen of the second device 120 and the second device 120 is inserted in the lumen of the first device 110 and out of the hole 112 of the first device 110 to form the Y-shaped flow diversion device 100 as shown in FIG. 8. The Y-shaped flow diversion device 100 now includes a proximal limb 101 and two distal limbs 102, 103. The proximal limb 101 comprises two layers due to the first device 110 and the second device 120 overlapping each other and the distal limbs 102, 103 each only have a single layer.

Figure 9:
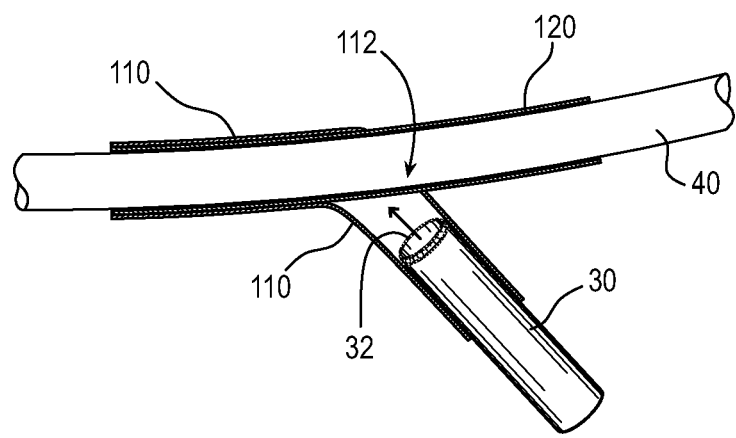
FIG. 9 illustrates a cross section view of a process of creating a hole or round cut-out from the second tubular flow diversion device of FIG. 8 to make a Y-shaped flow diversion device according to one embodiment of the present disclosure.

FIG. 9 illustrates a cross section view of a hole 122 or round cut-out being made in the second device 120. The cutting device 30 is inserted into the distal end 114 of the first device 110 and the sharp end of the cutting device 30. The cutting device 30 is rotated, thus creating the hole 122 in the second device 120. The plastic tube 40 is maintained in the second device 120 during the cutting process to provide support for the cutting device 30. The hole 122 in the second device 120 aligns with the lumen of a distal portion (e.g., the distal limb 103) of the first device 110.

Figure 10:
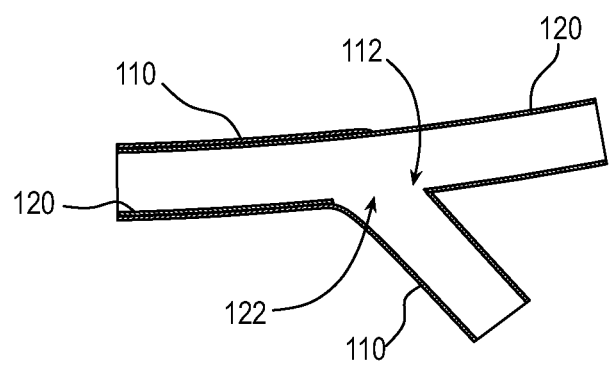
FIG. 10 illustrates a cross section view of a process of welding free wire ends of the Y-shaped flow diversion device of FIG. 9 according to one embodiment of the present disclosure.

FIG. 10 illustrates a cross section view of the Y-shaped flow diversion device 100 after the cut-out 122 has been made in the second device 120. After the cut-out 122 is completed, any free wire ends that were made from cutting the holes 112, 122 may be joined together using laser spot welding to weld free wire ends to adjacent wires. Other suitable methods may also be used to couple the free wire ends. Coupling (e.g., welding) of the free ends to adjacent wires further enhances the Y-shaped flow diversion device's 100 stability and strength. In some embodiments, the laser spot welding may be performed under a microscope.

Figure 11:
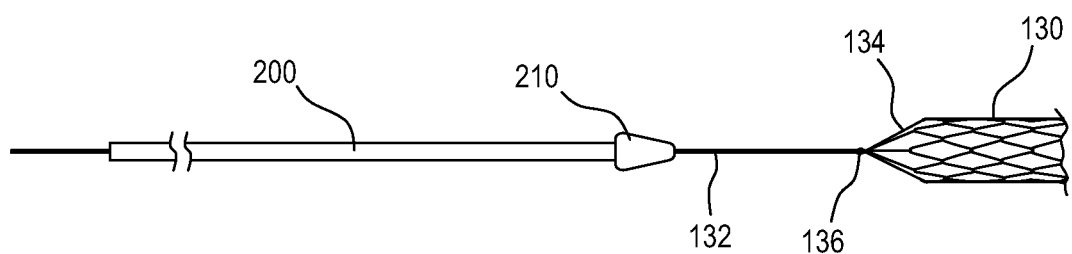
FIG. 11 illustrates a Y-shaped flow diversion device deployed in a catheter according to one embodiment of the present disclosure.

FIG. 11 illustrates the Y-shaped flow diversion device 100 constrained in a catheter 200 or flexible hypotube. The catheter 200 contains the distal ends 114, 124 (see FIGS. 12 and 13) of the Y-shaped flow diversion device 100 and guides the distal limbs 102, 103 over guidewires into the distal arteries of a branch point. The distal limbs 102, 103 are constrained by distal olives 210.

In some embodiments, the Y-shaped flow diversion device 100 may include an anchor stent 130 attached to a guidewire 132 and extend forwardly from a distal end 114, 124 of one of the distal limbs 102, 103. With reference to FIG. 11, the anchor stent 130 is a generally tubular-shaped, self-expanding mesh structure. The anchor stent 130 includes a plurality of connector struts 134 coalescing to a strut tip 136 at which the guidewire 132 is attached. In some embodiments, the anchor stent 130 may also include radiopaque markers on an end opposite the connector struts 134. In use, the anchor stent 130 provides a means to secure in place the Y-shaped flow diversion device 100 to ensure proper treatment is provided for the aneurysm 10. Additional information regarding the anchor stent 130 may be found in U.S. Pat. No. 10,022,251, which is hereby incorporated by reference in its entirety.

Figure 12:
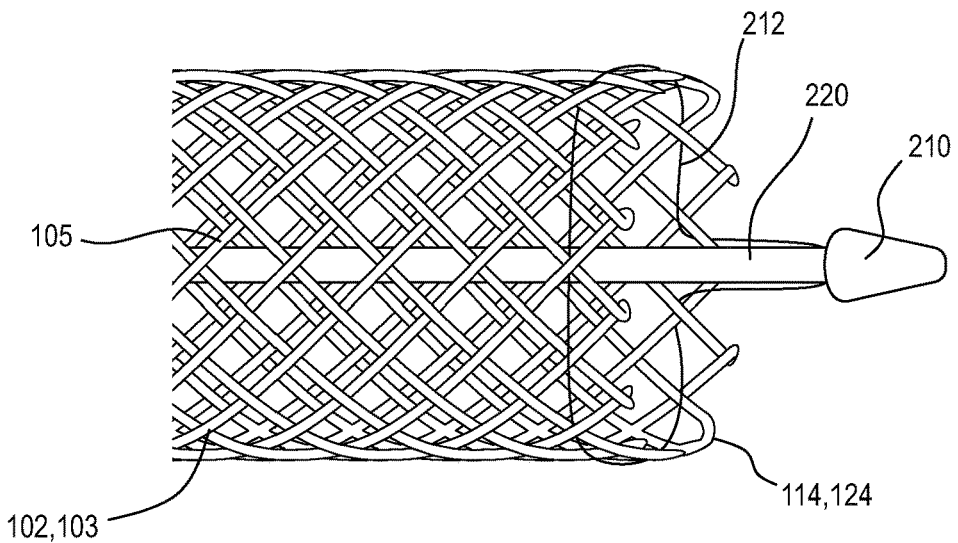
FIG. 12 illustrates a detailed side view of a distal limb of a Y-shaped flow diversion device in an unconstrained configuration according to one embodiment of the present disclosure.
Figure 13:
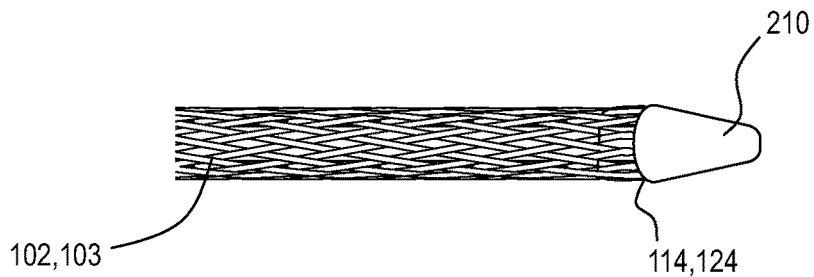
FIG. 13 illustrates a detailed side view of a distal limb of a Y-shaped flow diversion device in a constrained configuration according to one embodiment of the present disclosure.

FIGS. 12 and 13 illustrate a detailed view of one of the distal limbs 102, 103 of the Y-shaped flow diversion device 100 unconstrained by the distal olive 210. A tiny wire 220 or polyvinyl alcohol (PVA) cable may pass through interstices between the wire elements 105 near the distal end 114, 124 of the distal limb 102, 103. FIG. 13 illustrates a detailed view of one of the distal limbs 102, 103 of the Y-shaped flow diversion device 100 constrained by the distal olive 210. The wire/cable 220 is tightened down to collapse the distal limb 102, 103. A wire 212 may be used to constrain the distal end 114, 124 of the distal limbs 102, 103. The wire 212 may be woven between the interstices of the wire elements 105. In the illustrated embodiment, the wire 212 is only at the distal end 114, 124, however, the wire 212 may wrap and extend along the distal limbs 102, 103. This wire/cable 220 can be released mechanically or electrolytically, thus allowing the distal limb to expand.

Figure 14:
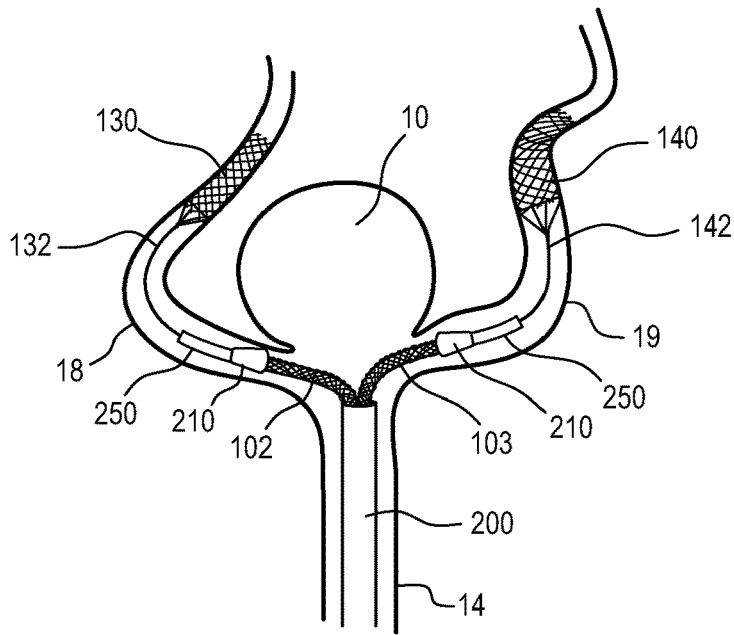
FIG. 14 illustrates a Y-shaped flow diversion device being deployed at a branch point aneurysm according to one embodiment of the present disclosure.

FIGS. 14-18 illustrate the process of placing the Y-shaped flow diversion device 100 to treat a branch point aneurysm 10. FIG. 14 illustrates a large wide-neck branch point aneurysm 10. The Y-shaped flow diversion device 100 is advanced into place by the catheter 200, such as a trackable 4-5 French intracranial guiding catheter. A couple of guidewires 132, 142, such as 0.014 inch anchor exchange wires are deployed from within both distal limbs 102, 103 of the Y-shaped flow diversion device 100 to provide extra support during delivery of the Y-shaped flow diversion device 100. In some embodiments, the guidewires 132, 142 may be anchor exchange wires that are coupled to anchor stents 130, 140. The distal limbs 102, 103 of the Y-shaped flow diversion device 100 are advanced into place along the guidewires 132, 142, each distal limb 102, 103 constrained by the distal olives 210.

Figure 15:
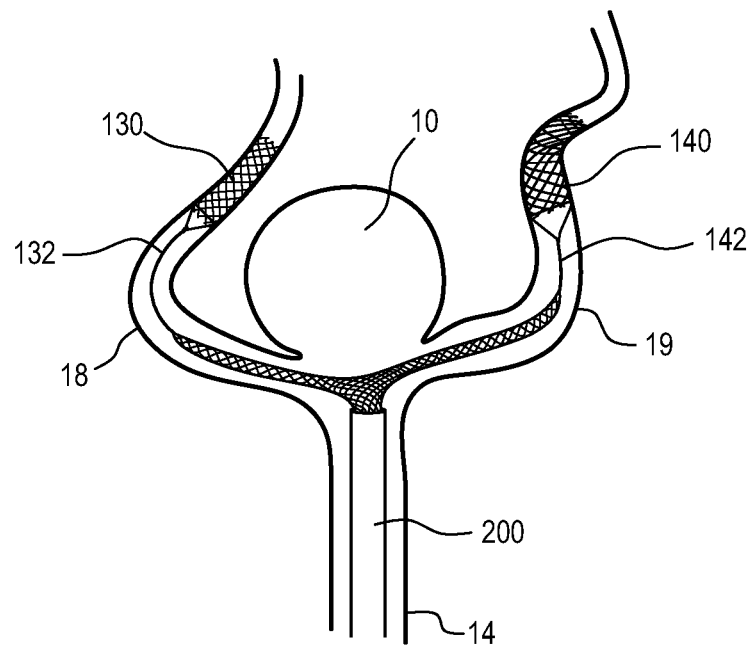
FIG. 15 illustrates a Y-shaped flow diversion device being deployed at a branch point aneurysm with the Y-shaped flow diversion device in a constrained configuration according to one embodiment of the present disclosure.
Figure 16:
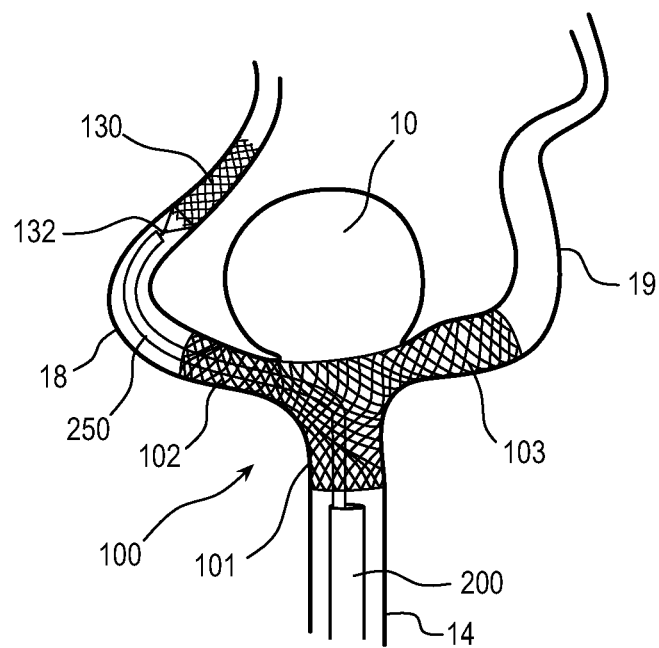
FIG. 16 illustrates a Y-shaped flow diversion device being deployed at a branch point aneurysm with the Y-shaped flow diversion device in an unconstrained configuration according to one embodiment of the present disclosure.

FIG. 15 illustrates the distal olives 210 of the distal limbs 102, 103 of the Y-shaped flow diversion device 100 detached and the distal limbs 102, 103 beginning to expand. FIG. 16 illustrates each distal limb 102, 103 fully expanded. After expansion, the guidewires 132, 142 and the anchor stents 130, 140 may be retrieved through 0.021 inch inner diameter microcatheters 250. FIG. 16 illustrates the anchor stent 140 removed and the anchor stent 130 in the process of being removed.

Figure 17:
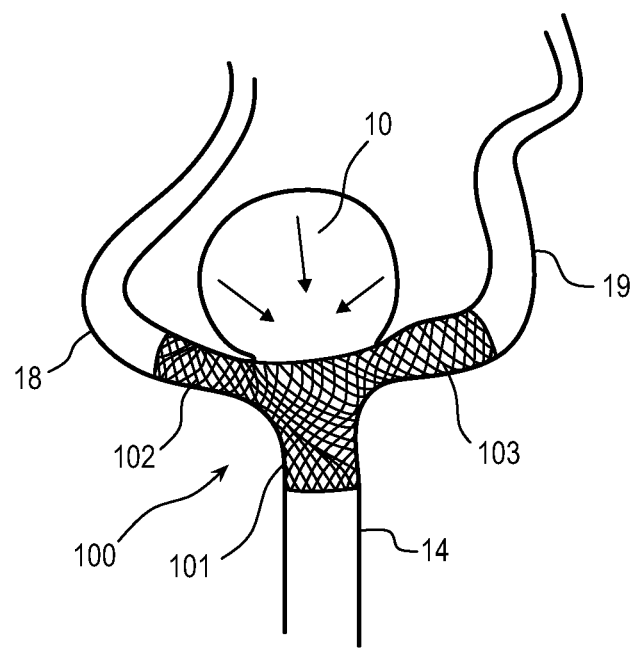
FIG. 17 illustrates a Y-shaped flow diversion device positioned at a branch point aneurysm according to one embodiment of the present disclosure.
Figure 18:
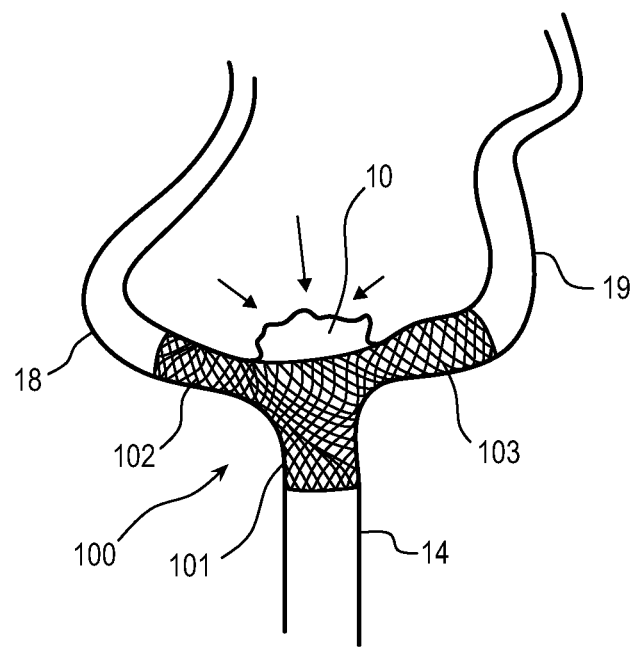
FIG. 18 illustrates the Y-shaped flow diversion device of FIG. 17 positioned at a branch point aneurysm three to six months after deployment of the Y-shaped flow diversion device.

FIG. 17 illustrates the Y-shaped flow diversion device 100 deployed at the branch point aneurysm 10. FIG. 18 illustrates the shrinking of the aneurysm 10 after the Y-shaped flow diversion device 100 is deployed three to six months.

In some embodiments, the braided-wire elements 105 of the Y-shaped flow diversion device 100 could be coated with anti-platelet/anti-thrombotic medication that might only require aspirin post operation.

The above-noted Y-shaped flow diversion device 100 might also find use treating peripheral aneurysms but also as a stent to treat branch point coronary and other arterial stenoses, and biliary duct stenoses, especially for cholangiocarcinoma (where radioactive isotope yttrium Y-90 may be incorporated into the device to provide radiation therapy). It may also be useful for branch point stenoses in the tracheobronchial tree.

The distal limbs 102, 103 of the Y-shaped flow diversion device 100 may be inserted over a 0.014 inch wire attached to an ultra-low profile balloon angioplasty catheter. The catheter may be composed of a coated flexible hypotube. In some embodiments, a distal balloon diameter would be no greater than 1.5 mm.

Figure 19:
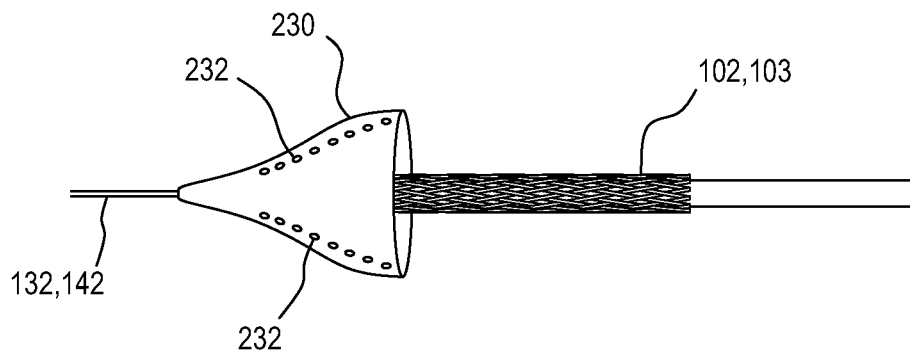
FIG. 19 illustrates a distal polymer hood that is disposed on one of two distal limbs of a Y-shaped flow diversion device according to one embodiment of the present disclosure.

In some embodiments, the distal limbs 102, 103 of the Y-shaped flow diversion device 100 may be constrained by a hood 230. FIG. 19 illustrates the distal polymer hood 230 that is attached to the catheter 200. The distal polymer hood 230 may be fabricated from PVA, polytetrafluoroethylene (PTFE), etc. The distal polymer hood 230 may comprise multiple lines of tiny perforations 232 that extend along the hood 230 as zones that split apart when the balloon is inflated. The lines of perforations 232 may be in a longitudinal direction of the hood 230. The Y-shaped flow diversion device 100 may comprise a pair of hoods 230, one for each distal limb 102, 103 of the Y-shaped flow diversion device 100.

Figure 20:
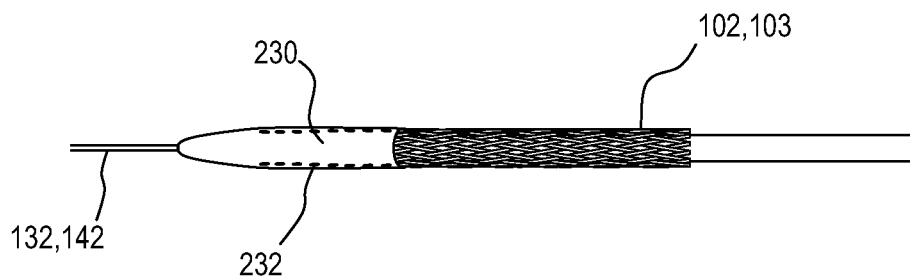
FIG. 20 illustrates a distal polymer hood constraining one of two distal limbs of a Y-shaped flow diversion device according to one embodiment of the present disclosure.

FIG. 20 illustrates the stretched and compressed distal ends 114, 124 of the distal limbs 102, 103 of the Y-shaped flow diversion device 100 placed under the distal hood 230 which is then shrink-wrapped on the distal end of the Y-shaped flow diversion device 100, locking it in a constrained state.

Figure 21:
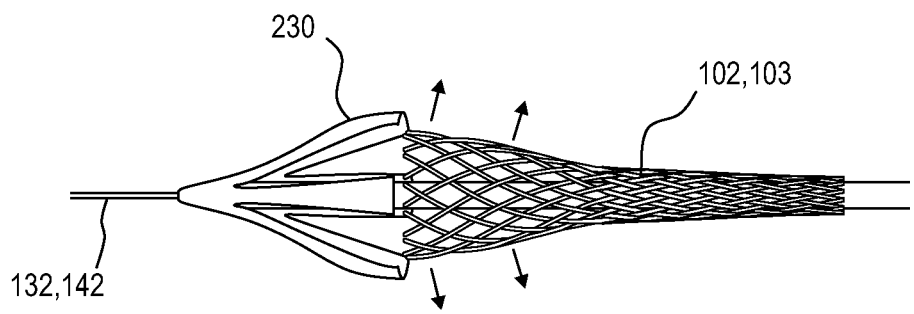
FIG. 21 illustrates the distal polymer hood of FIG. 20 split open to release the distal limb of the Y-shaped flow diversion device according to one embodiment of the present disclosure.

Once the Y-shaped flow diversion device 100 is in position, the balloon is inflated with saline or contrast, splitting open the polymer hood 230 along the lines of perforations 232, thus allowing the distal limbs 102, 103 of the Y-shaped flow diversion device 100 to expand as illustrated in FIG. 21.

FIG. 22 illustrates a Y-shaped flow diversion deployment system 300. The system 300 is disposed within a 4-5 French guide catheter 310. The system 300 is deployed over a couple of 0.014 inch guidewires 132, 142, with a guidewire 132, 142 disposed in each distal limb 102, 103 of the Y-shaped flow diversion device 100 and disposed in each vessel 18, 19. Each distal limb 102, 103 may have a circumferential flap 240 (similar to the distal olive 210) that keeps the distal limb 102, 103 constrained. The circumferential flap 240 may be fabricated from PTFE, PVA, or another similar material. A radiopaque marker 104 may be disposed at the crotch 106 (e.g., where the distal limbs 102, 103 converge) of the Y-shaped flow diversion device 100. The system 300 comprises a 4 French pusher catheter 320 to deploy the device.

FIG. 23 illustrates a cross section of the Y-shaped flow diversion deployment system 300. Each distal limb 102, 103 of the Y-shaped flow diversion device 100 is disposed over a 1.5 French catheter 330 within the 4-5 French guide catheter 310. FIG. 24 illustrates a cross section view of the 4-5 French guide catheter 310. The system 300 comprises a rubberized cuff 340 on the outside of the 4 French pusher catheter 320 that hugs the proximal limb 101 of the Y-shaped flow diversion device 100. FIG. 25 illustrates a cross section view of one of the distal limbs 102, 103 that is overlapped with the circumferential flap 240.

FIG. 26 illustrates a side detailed view of one of the distal limbs 102, 103 of the Y-shaped flow diversion device 100. The distal limbs 102, 103 of the Y-shaped flow diversion device 100 are released by pushing forward the 1.5 French catheter while holding the Y-shaped flow diversion device 100 stationary. The circumferential flaps 240 are configured to flip distally as shown in FIG. 27 allowing removal of the 1.5 French catheters. The proximal limb 101 of the Y-shaped flow diversion device 100 is released by holding the Y-shaped flow diversion device 100 stationary while withdrawing the 5 French guide catheter 200, as shown in FIGS. 28 and 29. Deployment of the Y-shaped flow diversion device 100 at the branch point aneurysm 10 involutes and occludes the aneurysm 10 over the next several months.

FIGS. 30-33 illustrate another embodiment of a Y-shaped flow diversion deployment system 400. FIG. 30 illustrates one of the distal limbs 102, 103 being secured and constrained to the distal end 412 of a delivery microcatheter or flexible hypotube 410 by a wire 420 coiled around the distal limb 102, 103. The Y-shaped flow diversion device deployment system 400 may comprise a pair of wires 420, with one wire being wrapped around a corresponding distal limb 102, 103. The wire 420 may be fabricated from Nitinol and have a diameter less than 0.0005 inch. The wire 420 may be wrapped around the distal limb 102, 103 between 8 and 20 times. The wire 420 may act as a spring with a diameter of approximately the outer diameter of the distal coated hypotube 410. The wire 420 would wrap snugly around the distal limb 102, 103 of the Y-shaped flow diversion device 100, thus constraining the distal limb 102, 103 and preventing it from expanding and detaching from its central hypotube 410.

Figure 31:
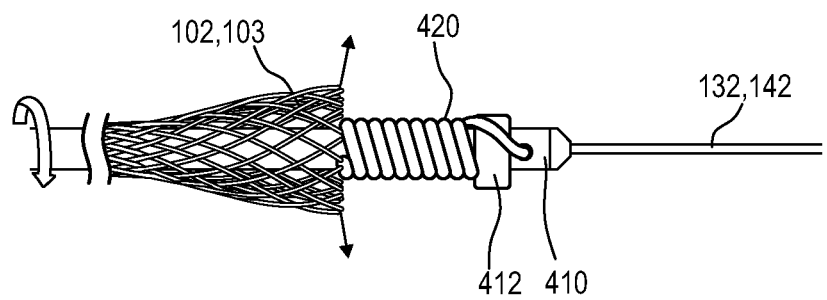
FIG. 31 illustrates the detachment of the distal limb of the Y-shaped flow diversion device of FIG. 30.

FIG. 31 illustrates the detachment of the Y-shaped flow diversion device 100 at a branch point aneurysm 10. To induce detachment, the wire 420 or the Nitinol spring, attached to the hypotube 410 just distal to the constrained flow diverter distal end 114, 124, would be screwed off the device by applying clockwise torque to the proximal end of the hypotube 410 using a torque device. The wire 420 (e.g., coil) unscrews from the distal limb 102, 103 of the Y-shaped flow diversion device 100 and branches distal to it. The wire 420 or coil hugs the outside of the internal catheter 330 avoiding difficulties in the removal of the internal catheters 330.

Figure 32:
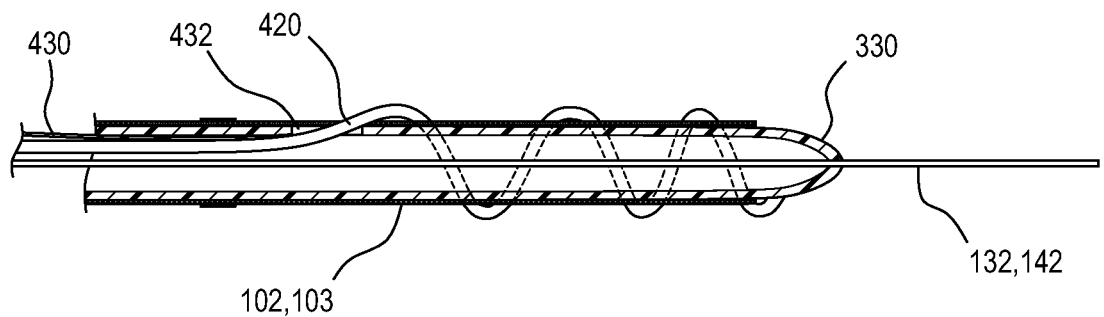
FIG. 32 illustrates one of two distal limbs of a Y-shaped flow diversion device being secured and constrained to the distal end of a delivery microcatheter or flexible hypotube by a wire coiled around the distal limb according to one embodiment of the present disclosure.
Figure 33:
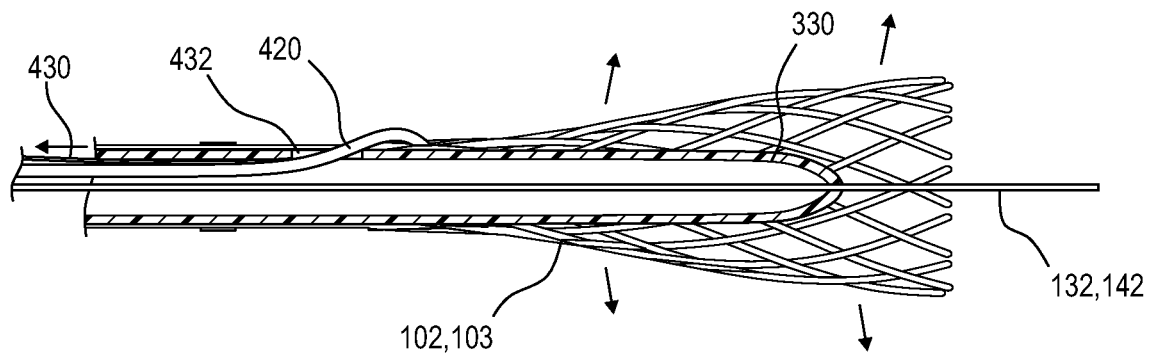
FIG. 33 illustrates the detachment of the distal limb of the Y-shaped flow diversion device of FIG. 32.

Alternately, the wire 420 or the Nitinol spring may be pulled off the constrained distal limb of the Y-shaped flow diversion device 100 by placing traction on a thin Nitinol wire 430 (or perhaps a thin Kevlar cable) running the length of the hypotube 410 exiting the lumen through an aperture 432 in the hypotube 410 either under or distal to the constrained device, as illustrated in FIGS. 32 and 33. If additional stability is needed in the wire 420 or spring, the wire 420 or spring could be affixed to the distal hypotube 410 and electrolytically detached.

It is intended that subject matter disclosed in any one portion herein can be combined with the subject matter of one or more other portions herein as long as such combinations are not mutually exclusive or inoperable. In addition, many variations, enhancements, and modifications of the concepts described herein are possible.

The terms and descriptions used above are set forth by way of illustration only and are not meant as limitations. Those skilled in the art will recognize that many variations can be made to the details of the above-described embodiments without departing from the underlying principles of the invention.

The invention claimed is:

1. A system for deploying a Y-shaped flow diversion device comprising:
   a guide catheter with a distal end and a proximal end, wherein the distal end of the guide catheter is configured to be advanced to a branch point aneurysm;
   two internal catheters disposed within the guide catheter;
   a pair of flaps; and
   an expandable Y-shaped flow diversion device disposed within the guide catheter in a constrained configuration, the Y-shaped flow diversion device comprising:
      a wire stent frame comprising a plurality of wire elements, the wire stent comprising a proximal limb and two distal limbs, wherein the proximal limb and the two distal limbs converge at a crotch of the wire stent frame,
   wherein the two internal catheters are disposed within the constrained proximal limb and the two internal catheters are each disposed in one of the two distal limbs,
   wherein each one of the flaps is disposed around a corresponding distal end of one of the two distal limbs of the Y-shaped flow diversion device to constrain the distal limbs of the Y-shaped flow diversion device, and
   wherein each one of the flaps are configured to flip distally to release the distal end of each distal limb of the Y-shaped flow diversion device, and
   wherein the two distal limbs are closer to the distal end of the guide catheter than the proximal limb when the Y-shaped flow division device is disposed within the guide catheter.

2. The system of claim 1, further comprising a pair of wires, each one of the wires wrapped around a corresponding distal limb of the two distal limbs of the Y-shaped flow diversion device to constrain the two distal limbs of the Y-shaped flow diversion device.

3. The system of claim 2, wherein a proximal end of the wire is disposed within one of the two internal catheters and a distal end of the wire exits through an aperture of the internal catheter and an interstice in a corresponding distal limb and wraps around the corresponding distal limb of the Y-shaped flow diversion device.

4. The system of claim 2, wherein each wire wraps around the corresponding distal limb of the Y-shaped flow diversion device between 8 and 20 times.

5. The system of claim 2, wherein the pair of wires are made of Nitinol.

6. The system of claim 1, further comprising a pusher catheter that is disposed within the guide catheter, wherein proximal ends of the two internal catheters are coupled to the pusher catheter.

7. The system of claim 6, wherein a distal end of the pusher catheter comprises a cuff that is disposed around a proximal end of the proximal limb of the Y-shaped flow diversion device.

8. The system of claim 1, wherein the Y-shaped flow diversion device is a single piece with a single layer of wires elements that are braided.

9. The system of claim 1, wherein the proximal limb of the flow diversion device comprises two layers of braided wire elements and the two distal limbs comprise a single layer of braided wire elements.

* * * * *